United States Patent
Hoffman-Zukowski et al.

(10) Patent No.: US 11,464,483 B2
(45) Date of Patent: Oct. 11, 2022

(54) OVERLAY SYSTEM INCLUDING A DETACHABLE HANDLE

(71) Applicant: Elekta Limited, Montreal (CA)

(72) Inventors: Marc Hoffman-Zukowski, Saint-Lambert (CA); Daniel Lodu, Stittsville (CA)

(73) Assignee: Elekta Limited, Montreal (CA)

( * ) Notice: Subject to any disclaimer, the term of this patent is extended or adjusted under 35 U.S.C. 154(b) by 319 days.

(21) Appl. No.: 16/361,139

(22) Filed: Mar. 21, 2019

(65) Prior Publication Data

US 2020/0297304 A1 Sep. 24, 2020

(51) Int. Cl.
*A61B 8/00* (2006.01)
*A61B 90/50* (2016.01)
*A61N 5/10* (2006.01)

(52) U.S. Cl.
CPC .............. *A61B 8/4209* (2013.01); *A61B 8/40* (2013.01); *A61B 8/4245* (2013.01); *A61B 90/50* (2016.02); *A61N 5/1049* (2013.01); *A61N 2005/1058* (2013.01)

(58) Field of Classification Search
CPC ..... A61B 8/4209; A61B 90/50; A61B 8/4245; A61B 8/40; A61N 2005/1058; A61N 5/1049
See application file for complete search history.

(56) References Cited

U.S. PATENT DOCUMENTS

| | | | |
|---|---|---|---|
| D264,874 S | 6/1982 | Augustsson et al. | |
| D286,073 S | 10/1986 | Russell | |
| 4,697,783 A | * 10/1987 | Kastendieck | A42B 3/042 2/10 |
| D386,584 S | 11/1997 | Frei | |

(Continued)

FOREIGN PATENT DOCUMENTS

| | | |
|---|---|---|
| CN | 205494276 | 8/2016 |
| CN | 113727652 A | 11/2021 |

(Continued)

OTHER PUBLICATIONS

Elekta: "Elect—Clarity", YouTube, 2016, https://www.youtube.com/watch?v=Qr8z5ELbQJw (Year: 2016).*

(Continued)

*Primary Examiner* — Christopher Koharski
*Assistant Examiner* — Taylor Deutsch
(74) *Attorney, Agent, or Firm* — Schwegman Lundberg & Woessner, P.A.

(57) ABSTRACT

An overlay system can include a substantially planar overlay base including a top side. The base can define a handle receptacle, for instance at a first end of the base. The handle receptacle can include a handle capture section optionally having a tapered profile. A centrally located elongated guide can extend longitudinally along the top side of the base to guide translational movement of the ultrasound probe holder along a longitudinal axis of the base. A handle can be configured to be attached and detached, by a user, with the (Continued)

handle receptacle of the base. The handle can define a channel optionally having a wedge profile. The wedge profile of the handle can correspond to the tapered profile of the handle receptacle. Engagement of the channel to the capture section of the handle receptacle can attach the handle to the base.

20 Claims, 7 Drawing Sheets

(56) References Cited

U.S. PATENT DOCUMENTS

| | | | |
|---|---|---|---|
| D393,069 S | 3/1998 | Jope | |
| D463,858 S | 10/2002 | Sherrod et al. | |
| D709,180 S | 7/2014 | Rummery et al. | |
| D816,833 S | 5/2018 | Parkhurst | |
| D872,864 S | 1/2020 | Marcil | |
| 2004/0087851 A1 | 5/2004 | Lee | |
| 2009/0227874 A1 | 9/2009 | Suri et al. | |
| 2009/0308400 A1 | 12/2009 | Wilson et al. | |
| 2011/0170671 A1 | 7/2011 | Blyakher et al. | |
| 2013/0129047 A1* | 5/2013 | Lim | A61B 6/0407 5/601 |
| 2016/0280143 A1 | 9/2016 | Sato et al. | |
| 2019/0150617 A1* | 5/2019 | Lager | F16M 13/02 |
| 2019/0231304 A1 | 8/2019 | Marcil | |
| 2019/0374418 A1* | 12/2019 | Lam | A61G 7/053 |

FOREIGN PATENT DOCUMENTS

| | | |
|---|---|---|
| WO | 02061371 | 8/2002 |
| WO | WO-2020186340 A1 | 9/2020 |

OTHER PUBLICATIONS

"U.S. Appl. No. 29/635,182, Corrected Notice of Allowability dated Dec. 11, 2019", 4 pgs.
"International Application Serial No. PCT CA2020 000041, Invitation to Pay Additional Fees and Partial Search Report dated May 11, 2020", 2 pgs.
"International Application Serial No. PCT CA2020 000041, International Search Report dated Jun. 18, 2020", 4 pgs.
"International Application Serial No. PCT CA2020 000041, Written Opinion dated Jun. 18, 2020", 7 pgs.
"Chinese Application Serial No. 201910080350.6, Notification on Correction of Deficiencies dated Mar. 12, 2019", w Concise Statement of Relevance, 2 pg.
"U.S. Appl. No. 29/635,182, Non Final Office Action dated Apr. 26, 2019", 11 pgs.
"RayBoards for Butterfly Masks with L-Profiles", [Online] Retrieved from the Internet :https: www.bcc.taipeiRTproducts product_pp121a.html, (accessed Mar. 19, 2019), 1.
"U.S. Appl. No. 29/635,182, Response filed Aug. 12, 2019 to Non Final Office Action dated Apr. 26, 2019", 5 pgs.
"U.S. Appl. No. 29/635,182, Notice of Allowance dated Sep. 3, 2019", 7 pgs.
"U.S. Appl. No. 15/898,495, Response filed Feb. 9, 2021 to Restriction Requirement dated Dec. 14, 2020", 6 pgs.
"U.S. Appl. No. 15/898,495, Restriction Requirement dated Dec. 14, 2020", 6 pgs.
Bionix Radiation Therapy, "Comfort Hold Foot Positioner RT-6030-30-03", [Online], Retrieved from the Internet: <URL: www.BionixRT.com>, 2 pgs.
CDR Systems, "CDR Systems Precision Positioning Systems", [Online], Retrieved from the internet: <URL:www.cdrsys.ca>, 58 pgs.
Klarity, "R634-LCF Leg Positioner Set-Up", [Online], Retrieved from the lnternet:<URL: www.klaritymedical.com>, 1 pg.
"U.S. Appl. No. 15/898,495, Non Final Office Action dated Apr. 28, 2021", 18 pgs.
"Elekta—Electron Boost VersaHD", YouTube, [Online] Retrieved from the internet:https: www.youtube.com watch?v=htoFAd1ALw8andt=35s (Year: 2015), (2015).
"U.S. Appl. No. 15/898,495, Response filed Jul. 28, 2021 to Non Final Office Action dated Apr. 28, 2021", 13 pgs.
"U.S. Appl. No. 15/898,495, Final Office Action dated Aug. 19, 2021", 8 pgs.
"U.S. Appl. No. 15/898,495, Response filed Oct. 4, 2021 to Final Office Action dated Aug. 19, 2021", 10 pgs.
"International Application Serial No. PCT CA2020 000041, International Preliminary Report on Patentability dated Sep. 30, 2021", 9 pgs.
"U.S. Appl. No. 15/898,495, Advisory Action dated Nov. 18, 2021", 5 pgs.
"European Application Serial No. 20774739.5, Response to Communication persuant to Rules 161 and 162 filed Mar. 15, 2022", 8 pgs.
"U.S. Appl. No. 15/898,495, Non Final Office Action dated Aug. 1, 2022", 23 pgs.

* cited by examiner

USER-ATTACHING OR USER-DETACHING A HANDLE TO A BASE, INCLUDING INSERTING OR REMOVING A HANDLE END INTO OR OUT OF AN INSERTION SECTION OF A HANDLE RECEPTACLE OF THE BASE, AND TRANSLATING THE HANDLE END INTO OR OUT OF A CAPTURE SECTION OF THE HANDLE RECEPTACLE OF THE BASE.

OVERLAY SYSTEM INCLUDING A DETACHABLE HANDLE

CROSS-REFERENCE TO RELATED PATENT DOCUMENTS

This patent application is related to Marcil, U.S. patent application Ser. No. 15/898,495, entitled "PATIENT OVERLAY FOR ULTRASOUND POSITIONING DEVICE," filed on Feb. 17, 2018 which is hereby incorporated by reference herein in its entirety

TECHNICAL FIELD

This document pertains generally, but not by way of limitation, to a system for positioning an ultrasound device proximal to an anatomy of a patient.

BACKGROUND

Ultrasound devices (e.g., a probe, sensor, or the like) can be positioned proximate to an anatomy (e.g., a prostate, diaphragm, abdomen, or the like) of a patient. A device can hold the ultrasound device in a position proximate to the anatomy of the patient.

SUMMARY

The present inventors have recognized, among other things, that a problem to be solved can include attaching and detaching a handle from a portable overlay base without the use of tools. The portable overlay base can be used to provide rails usable to slidably move an ultrasound probe holder toward or away from a patient resting on the overlay base. Additionally, the present inventors have recognized, among other things, that a problem to be solved can include providing a handle that is detachable from the overlay base while having a resilient engagement between the handle and the base. Further, the present inventors have recognized, among other things, that a problem to be solved can include supporting an ultrasound device and facilitating the positioning of the ultrasound device proximate to an anatomy of the patient.

The present subject matter can help provide a solution to this problem, such as by providing an overlay system for providing a movable interface between an ultrasound probe holder and a couch for radiotherapy. The overlay system can include a substantially planar overlay base including a top side. The base can define a handle receptacle, for instance at a first end of the base. The handle receptacle can include a handle capture section optionally having a tapered profile. A centrally located elongated guide can extend longitudinally along the top side of the base to guide translational movement of the ultrasound probe holder along a longitudinal axis of the base. A handle can be configured to be attached and detached, by a user, with the handle receptacle of the base. The handle can define a channel optionally having a wedge profile. The wedge profile of the handle can correspond to the tapered profile of the handle receptacle. Engagement of the channel to the capture section of the handle receptacle can attach the handle to the base.

The engagement of the channel to the capture section can provide a resilient engagement between the handle and the base. In an example, a user can attach the handle with the base, and a patient can rest upon the base. The user can lift the handle, and move (e.g., adjust the position of) the base. For example, the user can adjust the position of the base by engaging with the handle. The handle can be removed to help transport of the system. The handle can be removed to help facilitate removal of the probe holder from the base. The handle can be removed to help facilitate cleaning (e.g., sanitizing or the like) of the system.

In some examples, a pin (e.g., a fastener or the like) can be engaged with the handle to attach the handle with the base. However, engaging the pin with the handle can be cumbersome, and can require the usage of tools (e.g., pliers, wrenches, screwdrivers, or the like). The engagement of the channel to the capture section of the handle receptacle can readily attach the handle with the base and facilitate readily attaching and detaching the handle from the base.

Additionally, the overlay system can include one or more indexed engagement features, and the engagement features can couple with a support for an ultrasound device. The indexed engagement features can allow a user to locate the ultrasound device in a plurality of positions, and the engagement features can allow a user to readily locate the ultrasound device in the same position with respect to the patient. In an example, a patient can undergo one or more medical procedures, for instance over the course of multiple days. The indexed engagement features can facilitate locating ultrasound device in the same position with respect to the patient during the one or more medical procedures.

Aspect 1 may include or use subject matter (such as an apparatus, a system, a device, a method, a means for performing acts, or a device readable medium including instructions that, when performed by the device, may cause the device to perform acts), such as may include or use an overlay system for providing a movable interface between an ultrasound probe holder and a couch for radiotherapy, the overlay system comprising: a substantially planar overlay base including a top side, the base defining a handle receptacle including a handle capture section having a tapered profile; a centrally located elongated guide extending longitudinally along the top side of the base to guide translational movement of the ultrasound probe holder along a longitudinal axis of the base; a handle configured to be attached and detached, by a user, with the handle receptacle of the base, wherein: the handle defines a channel having a wedge profile that corresponds to the tapered profile of the handle receptacle; engagement of the channel to the capture section of the handle receptacle attaches the handle to the base.

Aspect 2 may include or use, or may optionally be combined with the subject matter of Aspect 1, to optionally include or use wherein the handle receptacle includes an insertion section sized and shaped to accommodate an end of the handle during handle insertion and removal by the user.

Aspect 3 may include or use, or may optionally be combined with the subject matter of Aspect 2 to optionally include or use wherein the handle receptacle is configured to allow the handle to translate between the insertion section and the capture section.

Aspect 4 may include or use, or may optionally be combined with the subject matter of one or any combination of Aspects 2 or 3 to optionally include or use a locking plate having a lock body sized and shaped to cover the insertion section of the base while engaging the handle receptacle of the base to couple the locking plate to the base.

Aspect 5 may include or use, or may optionally be combined with the subject matter of Aspect 4 to optionally include or use wherein locking plate is sized and shaped to inhibit displacement of the handle with respect to the handle receptacle.

Aspect 6 may include or use, or may optionally be combined with the subject matter of one or any combination of Aspects 4 or 5 to optionally include or use wherein the lock body includes a first axis and a second axis that is perpendicular to the first axis, and the lock body is stiffer along the first axis than along the second axis.

Aspect 7 may include or use, or may optionally be combined with the subject matter of one or any combination of Aspects 4 through 6 to optionally include or use that wherein the locking plate includes at least one tab extending from lock body and configured to engage with the handle receptacle.

Aspect 8 may include or use, or may optionally be combined with the subject matter of Aspect 7 to optionally include or use wherein the tab includes a clip portion sized and shaped to receive an edge of the handle receptacle.

Aspect 9 may include or use, or may optionally be combined with the subject matter of one or any combination of Aspects 1 through 8 to optionally include or use wherein the handle receptacle is defined in the base proximate to a first end of the base.

Aspect 10 may include or use, or may optionally be combined with the subject matter of one or any combination of Aspects 1 through 9 to optionally include or use wherein the locking channel of the handle includes a curved first section that is thinner than a linear second section extending from the first section.

Aspect 11 may include or use, or may optionally be combined with the subject matter of Aspect 10 to optionally include or use that wherein the locking channel includes a linear third section extending from the first section, wherein: the linear second section extends from the curved first section in a first direction; and the linear third section extends from the curved first section in a second direction.

Aspect 12 may include or use, or may optionally be combined with the subject matter of one or any combination of Aspects 1 through 11 to optionally include or use wherein the base defines indexed engagement features that are configured to engage directly or indirectly with the couch, and further comprising a locking plate configured to engage with the handle receptacle of the base to couple the locking plate with the base, wherein the locking plate defines at least one of the indexed engagement features located so as to be aligned with a corresponding individual engagement feature of the base.

Aspect 13 may include or use, or may optionally be combined with the subject matter of one or any combination of Aspects 1 through 12 to optionally include or use wherein the handle includes a stop extending from the handle and configured to engage with the top side of the base to inhibit over-insertion of the handle with respect to the handle receptacle.

Aspect 14 may include or use, or may optionally be combined with the subject matter of one or any combination of Aspects 1 through 13 to optionally include or use wherein the stop is located on the handle proximate to the locking channel.

Aspect 15 may include or use, or may optionally be combined with the subject matter of one or any combination of Aspects 1 through 14 to optionally include or use wherein the locking channel is located proximate to an end of the handle.

Aspect 16 may include or use, or may optionally be combined with the subject matter of one or any combination of Aspects 1 through 15 to optionally include or use wherein the locking channel defines a curved wall extending toward an interior portion of the handle.

Aspect 17 may include or use subject matter (such as an apparatus, a system, a device, a method, a means for performing acts, or a device readable medium including instructions that, when performed by the device, may cause the device to perform acts), such as may include or use a method for using a patient therapy couch, the method comprising: user-attaching or user-detaching a handle to a base, including inserting or removing a handle end into or out of an insertion section of a handle receptacle of the base, and translating the handle end into or out of a capture section of the handle receptacle of the base.

Aspect 18 may include or use, or may optionally be combined with the subject matter of Aspect 17, to optionally include or use locating an overlay base on the couch.

Aspect 19 may include or use, or may optionally be combined with the subject matter of one or any combination of Aspects 17 or 18 to optionally include or use locating a locking plate proximate to the base; and engaging the locking plate with the handle receptacle, wherein the locking plate has a lock body sized and shaped to cover the insertion section of the handle receptacle.

Aspect 20 may include or use, or may optionally be combined with the subject matter of one or any combination of Aspects 17 through 19 to optionally include or use wherein the handle includes a channel having a wedge-shaped profile and the handle receptacle has a tapered profile that corresponds to the wedge-shaped profile.

Aspect 21 may include or use, or may optionally be combined with the subject matter of one or any combination of Aspects 17 through 20 to optionally include or use lifting the base with the handle.

Aspect 22 may include or use, or may optionally be combined with the subject matter of one or any combination of Aspects 17 through 21 to optionally include or use wherein user-detaching of the handle from the base includes: disengaging a locking plate from the handle receptacle; translating the handle from the capture section to the insertion section; and removing the handle from the handle receptacle.

Aspect 23 may include or use subject matter (such as an apparatus, a system, a device, a method, a means for performing acts, or a device readable medium including instructions that, when performed by the device, may cause the device to perform acts), such as may include or use an overlay system for providing a movable interface between an ultrasound probe holder and a couch for radiotherapy, the overlay system comprising: a substantially planar overlay base including a top side, the base defining a tool-less user-attachable and user-detachable handle means for carrying or positioning the overlay (e.g., such as may include a U-shaped handle, such as may include a channel); means for receiving the handle means (e.g., such as may include a handle receptacle that tapers from an insertion portion toward a capture portion); means for capturing the handle means (e.g., such as may include a narrower portion of the receptacle into which the handle slides); and means for guiding translational movement of the ultrasound probe holder along a longitudinal axis of the base (e.g., such as may include one or more centrally located elongated rails).

Aspect 24 may include or use, or may optionally be combined with any portion or combination of any portions of any one or more of Aspects 1 through 23 to include or use, subject matter that may include means for performing any one or more of the functions of Aspects 1 through 23.

Each of these non-limiting aspects can stand on its own, or can be combined in various permutations or combinations with one or more of the other aspects.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
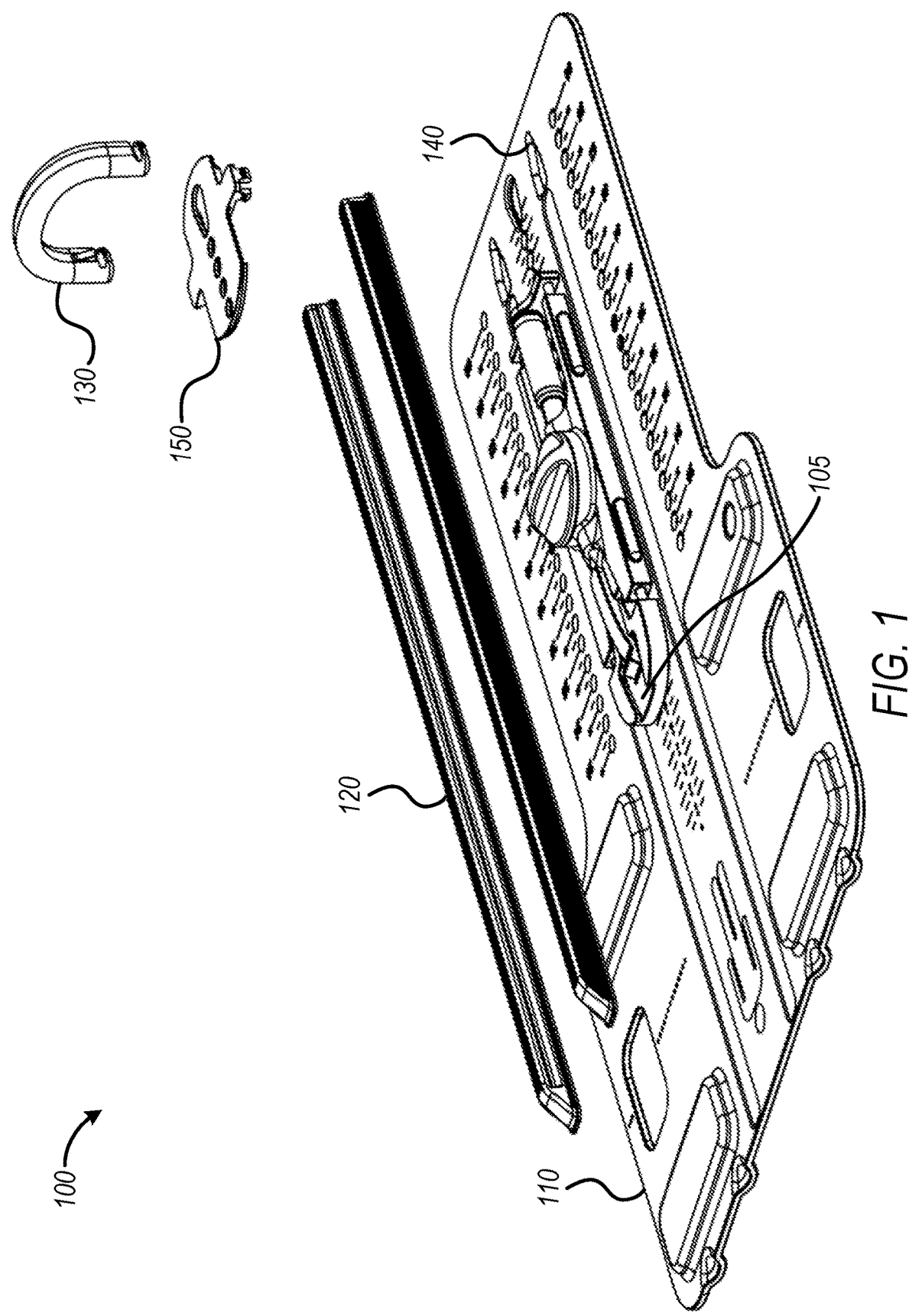
FIG. 1 is an exploded view of portions of an overlay system for providing a movable interface between an ultrasound probe holder and a couch for radiotherapy.

FIG. 1 is an exploded view of portions of an overlay system 100 for providing a movable interface between an ultrasound probe holder 105 and a couch for radiotherapy. For instance, the couch can include a platform sized and shaped to support a patient undergoing one or more medical procedures. The overlay system 100 can include an overlay base 110 and at least one guide 120. The overlay base 110 can be configured to couple with leg supports or knee supports, and the supports can help maintain the position of a patient while undergoing medical treatments. Additionally, the guide 120 can guide translational movement of the ultrasound probe holder 105 along a longitudinal axis of the base 110. Accordingly, the probe holder 105 can be repositioned with respect to the base 110 (and a patient when the patient is resting upon the overlay system 100).

The overlay system 100 can include a handle 130. The handle 130 can attach to, and detach from, the overlay base 110. The overlay base 110 can define at least one handle receptacle 140. The handle 130 can be engaged with the handle receptacle 140, such as to attach the handle 130 to the base 110. Additionally or alternatively, the handle 130 can be disengaged from the handle receptacle 140, such as to detach the handle 130 from the base 110.

Further, the overlay system 100 can include a locking plate 150. The locking plate 150 can be sized and shaped to engage with the base 110, such as by engaging with the handle receptacle 140. The engagement of the locking plate 150 with the handle receptacle 140 can couple the locking plate 150 to the base 110. As described in greater detail herein, the locking plate 150 can be sized and shaped to, (when the locking plate 150 is in place and engaged with the base 110) inhibit the handle 130 from transitioning from an attached configuration (e.g., when the handle 130 is engaged with the handle receptacle 140) to a detached configuration (e.g., when the handle 130 is disengaged from the handle receptacle 140).

Figure 2:
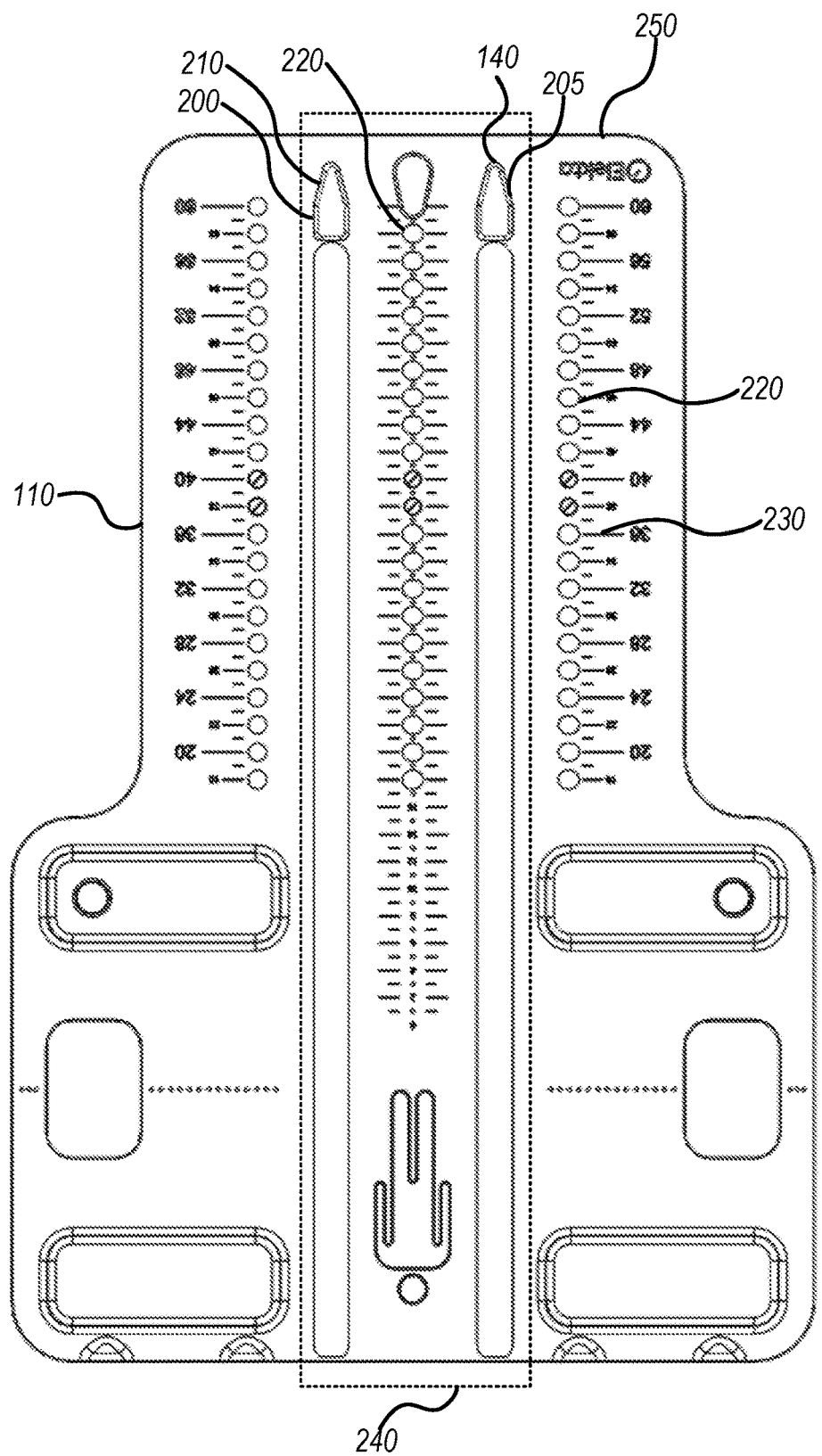
FIG. 2 is a top view of an example of an overlay base.

FIG. 2 is a top view of an example of the overlay base 110. As described herein, the base 110 can define the handle receptacle 140, which can extend partially or completely through the base 110, and the handle receptacle 140 can have receptacle walls 205.

The handle receptacle 140 can include (e.g., the base 110 can define) an insertion section 200 and a handle capture section 210. The insertion section 200 can be sized and shaped to accommodate an end of the handle 130 (e.g., the end 310 shown in FIG. 3), for instance when the handle 130 is inserted by a user (e.g., a technician, a nurse, a doctor, or the like) into the handle receptacle 140. Additionally or alternatively, the handle 130 can be removed from the handle receptacle 140, for instance when the handle 130 is located in the insertion section 200. The insertion section 200 can be larger (e.g., wider, or the like) than the capture section 210.

The handle 130 can translate between the insertion section 200 and the capture section 210. For instance, translating the handle 130 between the insertion section 200 and the capture section 210 can transition the handle 130 between the detached configuration and the attached configuration. In an example, a user can insert the handle 130 into the insertion section 200, and the user can translate (e.g., move, slide, push, pull, twist, or the like) the handle 130 to the capture section 210. The handle 130 can engage with the handle receptacle 140 when the handle 130 is in the capture section 220, and the handle 130 can be attached (e.g., coupled, secured, fastened, or the like) to the base 110.

The user can translate the handle 130 to the insertion section 200 from the capture section 210. The handle 130 can disengage from the handle receptacle 140 when the handle 130 is in the insertion section 200, and the handle 130 can be detached from the base 110. Accordingly, the handle 130 can be engaged to, or disengaged from, the base 110 without tools (e.g., a screwdriver, pliers, wrench, or the like).

The capture section 210 can be tapered. The insertion section 200 can be tapered. For example, a width the capture section 210 can have a first dimension proximate to the insertion section 200 (e.g., the capture section 210 can have an equal width to the insertion section 200 at the interface of the sections 200, 210). Additionally or alternatively, the insertion section 200 can have a second dimension when remote from the capture section 210 (e.g., the capture section 210 can have a smaller width, or neck down, at an end of the capture section 210 that is remote from the insertion section 200).

The base 110 can define indexed engagement features 220 such as for coupling the base 110 to an indexing bar (e.g., a bar including protrusions that provide a fixed reference point, for instance a reference point for positioning items on a couch). Each of the engagement features 220 can correspond to at least one corresponding marking 230 of the base 110. For example, the corresponding markings 230 can convey information about the spacing between adjacent engagement features 220, or about a cumulative distance from a reference marking and corresponding engagement feature 220. The engagement features 220 can engage directly to a couch, such as a couch, or indirectly to the couch, such as via an indexing bar.

The base 110 can include a central guide region 240, such as indicated by the dashed lines in FIG. 2. The central guide region 240 can include the one or more (e.g., a pair) of guide rails 120. Each of the guide rails 120 can include a V-shaped or other interior (e.g., inward-facing) groove and V-shaped or other exterior (e.g., laterally outward facing) groove. The interior grooves can face each other. An ultrasound probe holder, such as the ultrasound probe holder 105 (shown in FIG. 1) can engage with and can be guided in a longitudinal direction by the guide rails 120.

In FIG. 2, the handle receptacle 140 can be defined in the base 110 proximate to a first end 250 of the base 110. However, the handle receptacle 140 can be defined in different locations on the base 110. A plurality of handle receptacles 140 can be located around a periphery of the base 110. The handle receptacles 140 can be located within the central guide region 240. The handle receptacles 140 can be arranged in a geometric (e.g., circular) pattern to allow for repositioning the handle 130 in a plurality of positions with respect to the base 110.

Figure 3:
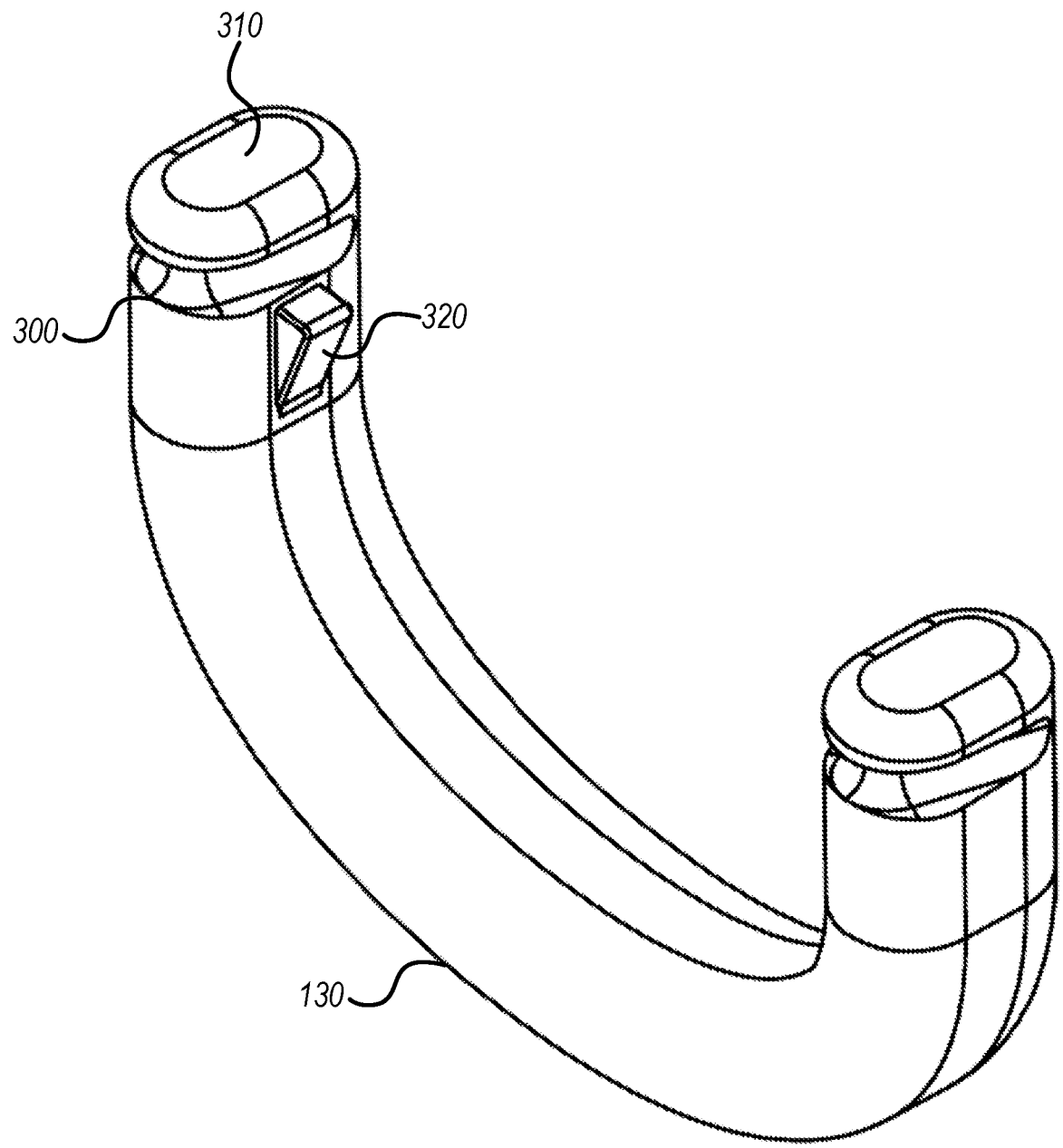
FIG. 3 is an isometric view of an example of a handle.

FIG. 3 is an isometric view of an example of the handle 130. The handle 130 can define a channel 300. The channel 300 can be sized and shaped to engage (e.g., receive) to a receptacle (e.g., the handle receptacle 140) of the base 110 (shown in FIG. 2). The channel 300 can engage to the capture section 210 of the handle receptacle 140 (shown in FIG. 2), and the engagement of the channel 300 with the capture section 210 can attach the handle 130 to the base 110. For instance, the receptacle walls 205 (shown in FIG. 2) can be received in the channel 300 and the reception of the walls 205 in the channel 300 can attach the handle 130 to the base 110.

An end 310 of the handle 130 can be sized and shaped to be inserted into the handle receptacle 140, for instance the end 310 can be inserted into the insertion section 200 of the handle receptacle 140. The handle 130 can include a stop 320, and the stop 320 can help inhibit or prevent over-insertion of the handle 130 into the handle receptacle 140. For instance, the stop 320 can engage with the base 110 and the engagement of the stop 320 with the base 110 can align the channel 300 with the handle receptacle 140. In an example, the stop 320 can be located on the handle 130 proximate to the channel 300, and the channel 300 can be located proximate to the end 310 of the handle 130 (e.g., the channel 300 can be located between the end 310 and the stop 320). The stop 320 can facilitate the alignment of the channel 300 with the walls 205 (shown in FIG. 2) of the handle receptacle 140, for instance to simplify engagement of the handle 130 with the handle receptacle 140.

The handle 130 can have any of a variety of profiles. As shown in FIG. 3, the handle 130 can be U-shaped and include a pair of ends 310. In another example, the handle 130 can be linear (e.g., a post) with a single end 310. As shown in FIG. 3, the handle 130 can have (but is not limited to) an oval cross-section. However, the handle 130 can include a circular cross-section, a rectangular cross-section, other geometric-shaped cross-section, or an irregular cross-section. Further, the overlay system 100 can include a plurality of handles 130, and the handles 130 can be located at one or more positions with respect to the base 110 (e.g., the base 110 can define a plurality of handle receptacles 140, for instance at a plurality of locations around a periphery of the base 110 or the central guide region 240.).

Figure 4:
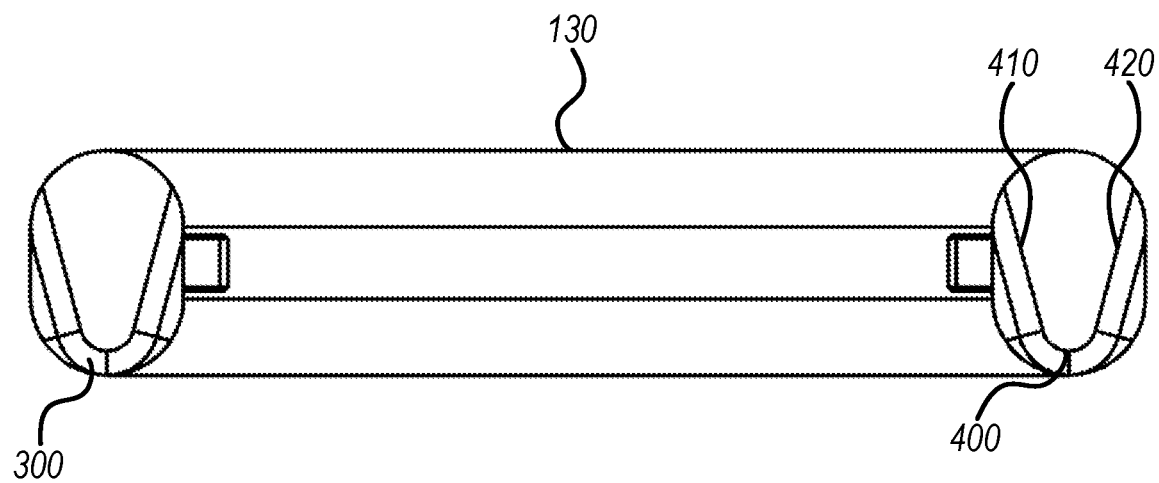
FIG. 4 is a bottom view of the handle of FIG. 3 with a portion of the handle hidden for clarity.

FIG. 4 is a bottom view of the handle 130 of FIG. 3 with a portion of the handle 130 hidden for clarity. As described herein, the handle 130 can include the channel 300. The channel 300 can have a wedge profile. The wedge profile of the channel 300 can correspond to the tapered profile of the capture section 210 (shown in FIG. 2). For instance, the channel 300 can include a curved first section 400, and a linear second section 410. The linear second section 410 can extend from the curved first section 400. Additionally, the curved first section 400 can be thinner than the linear second section 410 (e.g., a thickness of the channel 300 can be smaller in the curved first section 400 than the thickness of the channel 300 in the linear second section 410.

Further, the channel 300 can include a linear third section 420 extending from the curved first section 400. In an example, the linear third section 420 can extend from a different portion of the first section 400 than the linear second section 410. In some examples, the linear second section 410 can extend from the first section 400 in a first direction, and the linear third section 420 can extend from the first section 400 in a second direction. Optionally, the thickness of the channel 300 between the second section 410 and the third section 420 can be greater than the thickness of the channel 300 in the curved first section 400. The first section 400 can be linear, and the second section 410 and the third section 430 can be curved (or include combinations thereof).

Figure 5:
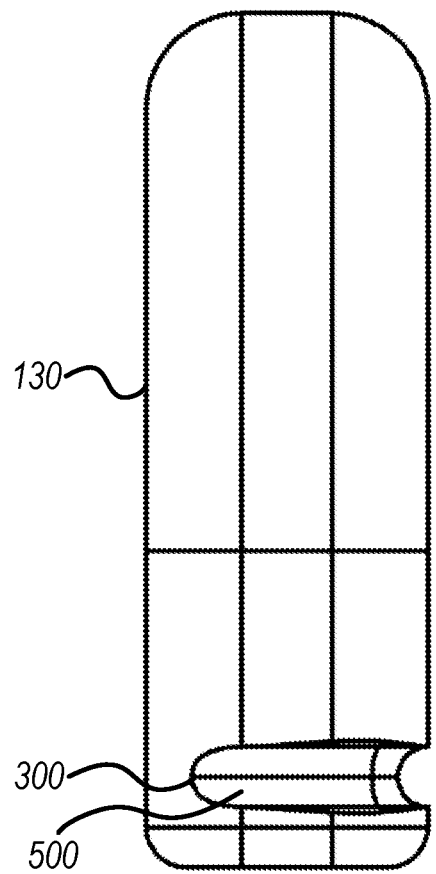
FIG. 5 is a side view of the handle of FIG. 3.

FIG. 5 is a side view of the handle 130 of FIG. 3. The channel 300 can be defined by channel walls 500. The channel walls 500 can have a curved profile, rectangular profile, other geometric-shaped profile, or an irregularly shaped profile. As shown in FIG. 5, the channel walls 500 include a curved (e.g., semicircle) profile. The profile of the channel walls 500 can correspond with the profile of the receptacle walls 205 of the handle receptacle 140 (shown in FIG. 2). Accordingly, the channel 300 can engage to the handle receptacle 140 (e.g., the capture section 210, shown in FIG. 2). The channel 300 can extend partially (or completely) around a perimeter of the handle 130.

Figure 6:
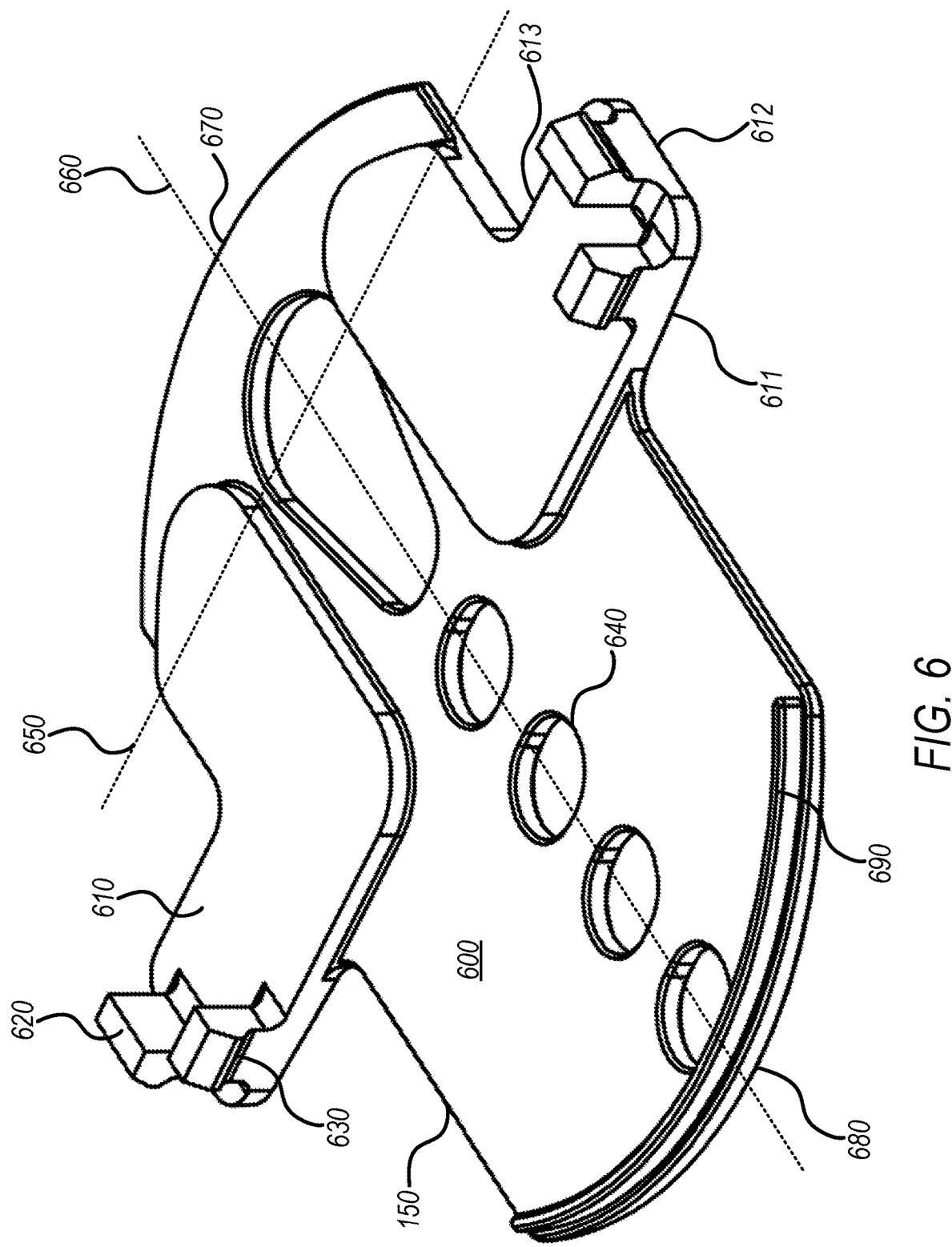
FIG. 6 is an isometric view of an example of a locking plate.

FIG. 6 is an isometric view of an example of the locking plate 150. The locking plate 150 can include a lock body 600, and the lock body 600 can be sized and shaped to cover a portion of the handle receptacle 140. The lock body 600 can include a wing 610, and the wing 610 can cover the insertion section 200 of the handle receptacle 140 (shown in FIG. 2). In this example, when the wing 610 covers the insertion section 200, the locking plate 150 can inhibit the translation of the handle 130 from the capture section 210 to the insertion section 200. For instance, the handle 130 can engage with the wing 610 and the wing 610 can inhibit (e.g., interfere, block, prevent, stop, or the like) the translation of the handle 130 with respect to the handle receptacle 140. The locking plate 150 can engage with the handle 130 (e.g., the wing 610 can be received in the channel 300) to enhance coupling of the handle 130 to the handle receptacle 140.

The locking plate 150 can include one or more (e.g., a pair) tabs 620. The tabs 620 can project from the lock body 600, for example the wing 610, and the tabs 620 can engage with the handle receptacle 140 to couple the locking plate 150 to the base 110 (shown in FIG. 1). Further, the tabs 620 can engage with other portions of the base 110 (e.g., the engagement features 220, shown in FIG. 2) to couple the locking plate 150 to the base 110. The tab 620 can include a clip 630, and the clip 630 can be sized and shaped to receive (e.g., capture, hold, grasp, retain, or the like) an edge of the handle receptacle 140 (e.g., a portion of the receptacle walls 205, shown in FIG. 2).

The tabs 620 can be located on two or more sides of the wing 610, for instance a first side 611 and a second side 612 of the wing 610. Accordingly, the tabs 620 can engage with two or more sides of the handle receptacle 140. The tabs 620 can be located on the first side 611, the second side 612, and a third side 613 of the wing 610. Accordingly, the tabs 620 can engage with three sides of the handle receptacle 140 (e.g., three sides of the insertion section 200). Optionally, the handle receptacle 140 can include a circular or oblong profile, and the tabs 620 can engage with the circular or oblong profile of the handle receptacle 140.

The locking plate 150 can define engagement features 640. The engagement features 640 of the locking plate 150 can be located to align with the engagement features 220 of the base 110 (shown in FIG. 2), for instance when the locking plate 150 is coupled to the base 110. The locking plate 150 can include a first axis 650, and a second axis 660 that can be perpendicular to the first axis 650. The locking plate 150 can be stiffer along the first axis 650 than along the second axis 660 (e.g., the locking plate 150 can be more flexible along the second axis 660 than along the first axis 650). Accordingly, the amount of force necessary to elastically deform (e.g., flex, bend, displace, or the like) the lock body 600 along the second axis 660 can be less than the amount of force necessary to elastically deform the lock body 600 along the first axis 650. The engagement features 640 can be sized, shaped, or located to facilitate the decreased stiffness of the locking plate 150 along the second axis 660.

Configuring the locking plate 150 to be stiffer along the first axis 650 in comparison to the second axis 660 can improve the coupling of the locking plate 150 to the overlay base 110. In an example, increasing the stiffness of the locking plate 150 along the first axis 650 can increase the amount of force necessary to disengage the locking plate 150 from the handle receptacle 140. In another example, decreasing the stiffness of the locking plate 150 along the second axis 660 can decrease the amount of force necessary to disengage the locking plate 150 from the handle receptacle 140.

For instance, a user can grasp a first end 670 of the locking plate 150 and pull on the first end 670 to disengage the locking plate 150 from the handle receptacle 140. The user can remove the locking plate 150 from the base 110 by disengaging the locking plate 150 from the handle receptacle 140. Configuring the locking plate 150 to be less stiff along the second axis 660 can facilitate disengaging the locking plate 150 from the handle receptacle 140. In an example, the tabs 620 can be located on the sides 611, 612 of the wing 610, and the tabs 620 (or the clip 630) can act as a fulcrum. Pulling on the first end 670 can disengage the clips 630 from the handle receptacle 140, for instance to help allow the locking plate 150 to be removed from the base 110. Configuring the locking plate 150 to be less stiff along the second axis 660 can improve the amount of leverage a user has to disengage the locking plate 150 from the handle receptacle 140 (e.g., decrease user effort to disengage the locking plate 150 from the handle receptacle 140).

The clip 630 can be used as a pivot point the stabilized the release of the tabs 620 from the handle receptacle 140. For example, a user can pull on the first end 670, and a lip 690 of the locking plate 150 can engage with the base 110. Adjusting the dimension between the clip 630 and the lip 690 can adjust the amount of force necessary to disengage the locking plate 150 from the handle receptacle 140.

In another example, the tabs 620 can be located on the side 613 of the wing 610. Locating the tabs 620 on the side 613 can increase the amount of force necessary to disengage the locking plate 150 from the handle receptacle 140, for instance because of reduced leverage being generated by a force applied to the first end 670. Accordingly, the amount of force necessary to disengage the locking plate 150 from the handle receptacle 140 can be tuned depending upon the location of the tabs 620 (or the clips 630). For example, the amount of effort needed by a user to disengage the locking plate 150 from the handle receptacle 140 cane be tuned by varying the location of the tabs 620 (or the clips 630).

Additionally, the location of the tabs 620 can be adjusted to prevent unintended removal of the locking plate 150 from the base 110. In an example, placing the tabs 620 on the sides 611, 612 of the wing 610 can inhibit disengaging the locking plate 150 by pulling on the wing 610. Further, locating the tabs 620 on the sides 611, 612 can inhibit disengaging the locking plate 150 by pulling on a second end 680 of the locking plate 150. Still further, locating the tabs 620 on the sides 611, 612 can allow the locking plate 150 to disengage from the handle receptacle 140, for instance by a user pulling on the first end 670 of the locking plate 150. Accordingly, locating the tabs 620 on the sides 611, 612 can facilitate disengaging the locking plate 150 from the handle receptacle 140 in a single direction (e.g., by pulling on the first end 670).

Figure 7:
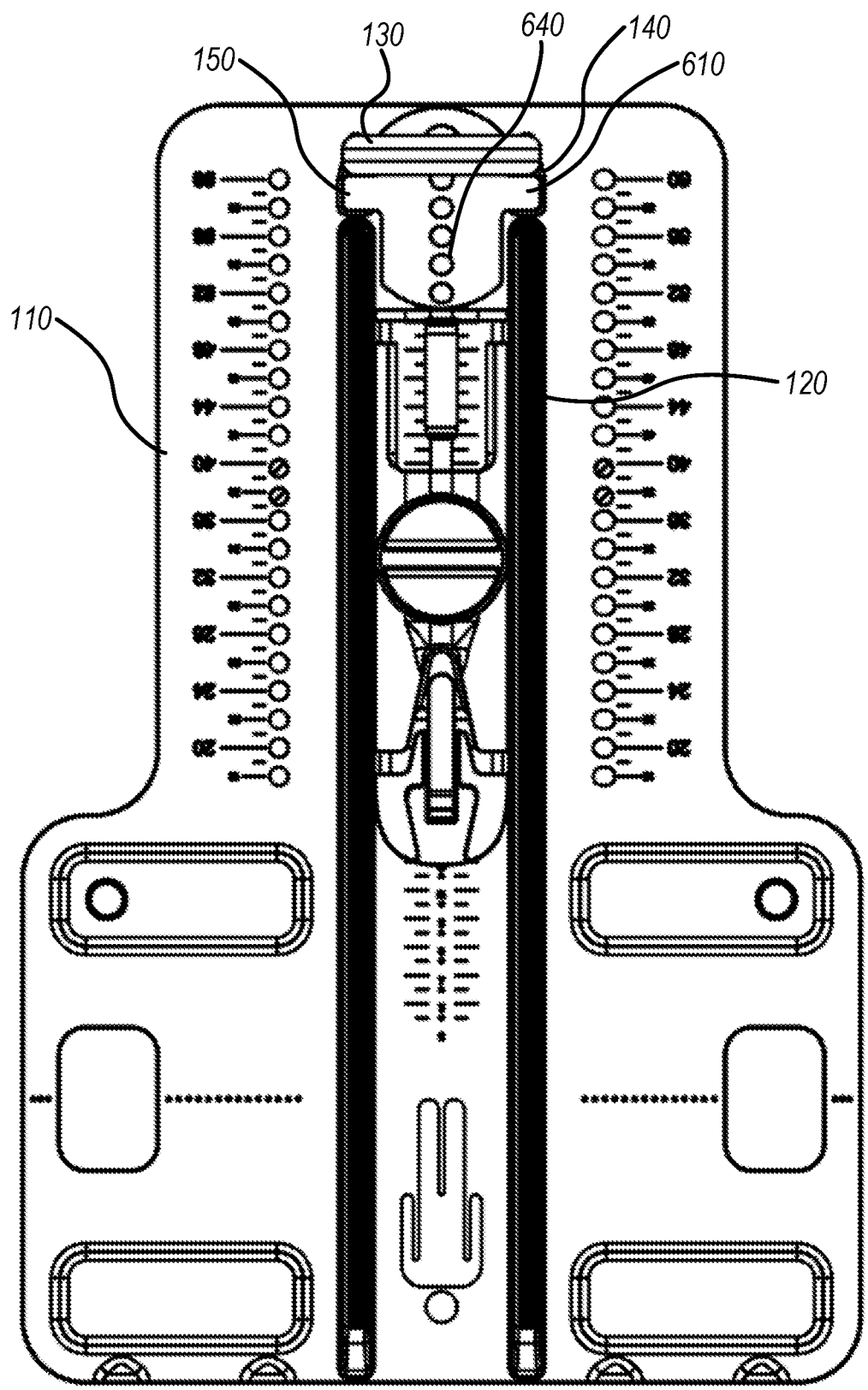
FIG. 7 is a top view of the overlay system of FIG. 1.

FIG. 7 is a top view of the overlay system 100 of FIG. 1. As described herein, the handle 130 can be attached to the base 110, for instance by engaging the handle 130 with the handle receptacle 140. Additionally, the locking plate 150 can be engaged with the handle receptacle 140 (also shown in FIGS. 1 and 2) to couple the locking plate 150 to the overlay base 110. Further, the locking plate 150 can help secure the handle 130 to the base 110, for instance by preventing the translation of the handle 130 with respect to the handle receptacle 140. Still further, the engagement features 640 of the locking plate 150 can align with the engagement features 220 of the base 110 (shown in FIG. 2) when the locking plate 150 is coupled to the base 110.

In some examples, the wing 610 can cover a portion of the handle receptacle 140 (e.g., the insertion section 200), and accordingly prevent the translation of the handle 130 with respect to the handle receptacle 140. Additionally, the wing 610 can be sized and shaped to be located between the handle 130 and the guide 120 when the locking plate 150 is coupled to the base 110. Further, the locking plate 150 can be sized and shaped to extend into a region between the guides 120. The locking plate 150 can engage with the ultrasound probe holder 105, for instance to inhibit the ultrasound probe holder 105 from disengaging from the guides 120. Still further, the locking plate 150 can inhibit the ultrasound probe holder 105 from interacting with a user of the system 100, for instance when a user is grasping the handle 130. Accordingly, the locking plate 150 can be configured to stop the translation of the ultrasound probe holder 105 with respect to the guides 120.

Figure 8:
FIG. 8 is a flowchart diagram of method for using a patient therapy couch.

FIG. 8 is a flowchart diagram of a method for using a patient therapy couch. In describing the method 800, reference is made to one or more components, features, functions and operations previously described herein. Where convenient, reference is made to the components, features, operations and the like with reference numerals. The reference numerals provided are exemplary and are not exclusive. For instance, components, features, functions, operations and the like described in the method 800 include, but are not limited to, the corresponding numbered elements provided herein and other corresponding elements described herein (both numbered and unnumbered) as well as their equivalents.

At 800, a handle 130 can be user-attached, or user-detached, to a base 110. An end 310 of the handle 130 can be inserted into (or removed out of) an insertion section 200 of a handle receptacle 140 of the base 110. The handle end 310 can be translated into (or out of) a capture section 210 of the handle receptacle 140 of the base 110.

Several options for the method 800 follow. The base 110 can be located on the couch. The base 110 can be lifted with the handle 130. A locking plate 150 can be located proximate to the base 110. The locking plate 150 can be engaged with the handle receptacle 140. The locking plate 150 can have a lock body 600 sized and shaped to cover the insertion section 200 of the handle receptacle 140. The handle 130 can include a channel 300 optionally having a wedge-shaped profile. The handle receptacle 140 can have a tapered profile that corresponds to the wedge-shaped profile of the channel 300.

User-detaching of the handle 130 from the base 110 can include disengaging the locking plate 150 from the handle receptacle 140. The handle 130 can be translated from the capture section 210 to the insertion section 200. The handle 130 can be removed from the handle receptacle 140.

VARIOUS NOTES

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An overlay system for providing a movable interface between an ultrasound probe holder and a couch for radiotherapy, the overlay system comprising:
   a planar overlay base including a top side, the planar overlay base defining a handle receptacle extending from the top side of the planar overlay base, wherein the handle receptacle comprises an insertion section and a handle capture section having a taper, wherein:
      the handle capture section has a first lateral dimension proximate the insertion section;
      the handle capture section has a second lateral dimension remote from the insertion section; and
      the first lateral dimension is greater than the second lateral dimension to taper a receptacle opening defined by the handle capture section and narrow the receptacle opening in a direction away from the insertion section when viewed toward the top side of the planar overlay base;
   a centrally located elongated guide extending longitudinally along the top side of the planar overlay base to guide translational movement of the ultrasound probe holder along a longitudinal axis of the planar overlay base; and
   a handle configured to be attached and detached, by a user without requiring using a tool, with the handle receptacle of the planar overlay base, wherein:
      the handle defines a channel having a wedge profile that corresponds to the taper of the handle receptacle; and engagement of the channel to the handle capture section of the handle receptacle attaches the handle to the top side of the planar overlay base.

2. The overlay system of claim 1, wherein one of the handle capture section and the insertion section is closer to an edge of the planar overlay base than the other of the handle capture section and the insertion section.

3. The overlay system of claim 2, wherein the handle receptacle is configured to allow the handle to translate between the insertion section and the handle capture section.

4. The overlay system of claim 2, further comprising a locking plate having a lock body sized and shaped to cover the insertion section of the planar overlay base while engaging the handle receptacle of the planar overlay base to couple the locking plate to the planar overlay base.

5. The overlay system of claim 4, wherein the locking plate is sized and shaped to inhibit displacement of the handle with respect to the handle receptacle.

6. The overlay system of claim 4, wherein the lock body includes a first axis and a second axis that is perpendicular to the first axis, and the lock body is stiffer along the first axis than along the second axis.

7. The overlay system of claim 4, wherein the locking plate includes at least one tab extending from the lock body and configured to engage with the handle receptacle.

8. The overlay system of claim 7, wherein the at least one tab includes a clip portion sized and shaped to receive an edge of the handle receptacle.

9. The overlay system of claim 1, wherein the handle receptacle is defined in the planar overlay base proximate to a first end of the planar overlay base, and the handle capture section tapers toward the first end of the planar overlay base to narrow the receptacle opening of the handle capture section with respect to the receptacle opening of the insertion section when viewed toward the top side of the planar overlay base.

10. The overlay system of claim 1, wherein the channel of the handle includes a curved first section that is thinner than a linear second section extending from the curved first section.

11. The overlay system of claim 10, wherein the channel includes a linear third section extending from the curved first section, wherein:
   the linear second section extends from the curved first section in a first direction; and
   the linear third section extends from the curved first section in a second direction.

12. The overlay system of claim 1, wherein the overlay system defines a plurality of indexed engagement features that are configured to engage directly or indirectly with the couch, and further comprising a locking plate configured to engage with the handle receptacle of the planar overlay base to couple the locking plate with the planar overlay base, wherein the locking plate defines at least one of the plurality of indexed engagement features located so as to be aligned with a corresponding individual one of the plurality of indexed engagement features on the planar overlay base.

13. The overlay system of claim 1, wherein the handle includes a stop extending from the handle and configured to engage with the top side of the planar overlay base to inhibit over-insertion of the handle with respect to the handle receptacle.

14. The overlay system of claim 13, wherein the stop is located on the handle proximate to the channel.

15. The overlay system of claim 1, wherein the channel is located proximate to an end of the handle, and the channel is configured to engage with receptacle walls of the handle receptacle.

16. The overlay system of claim 1, wherein the channel defines a curved wall extending toward an interior portion of the handle.

17. A method for using a patient therapy couch, the method comprising:
   user-attaching or user-detaching a handle to a base of an overlay system, including inserting or removing a handle end into or out of an insertion section of a handle receptacle of the base, and translating the handle end into or out of a handle capture section of the handle receptacle of the base; and
   wherein the overlay system includes:
      the base, and the base is a planar overlay base including a top side, the base defining the handle receptacle extending from the top side of the base, the handle receptacle including the handle capture section having a tapered profile and the insertion section, wherein:
         the handle capture section has a first lateral dimension proximate the insertion section;
         the handle capture section has a second lateral dimension remote from the insertion section; and
         the first lateral dimension is greater than the second lateral dimension to provide a narrowing taper to a receptacle opening of the handle capture section when viewed toward the top side of the base;
      a centrally located elongated guide extending longitudinally along the top side of the base to guide translational movement of an ultrasound probe holder along a longitudinal axis of the base; and
      the handle, wherein the handle is configured to be attached and detached, by a user without requiring using a tool, with the handle receptacle of the base, wherein:
         the handle defines a channel having a wedge profile that corresponds to the tapered profile of the handle receptacle; and
         engagement of the channel to the handle capture section the capture section of the handle receptacle attaches the handle to the top side of the base.

18. The method of claim 17, further comprising locating the base on the patient therapy couch.

19. The method of claim 17, further comprising:
   locating a locking plate proximate to the base; and
   engaging the locking plate with the handle receptacle, wherein the locking plate has a lock body sized and shaped to cover the insertion section of the handle receptacle.

20. The method of claim 17, wherein the user-detaching of the handle from the base includes:
   disengaging a locking plate from the handle receptacle;
   translating the handle from the handle capture section to the insertion section; and
   removing the handle from the handle receptacle.

* * * * *